United States Patent [19]

Cohen

[11] Patent Number: 4,703,757
[45] Date of Patent: Nov. 3, 1987

[54] OPTICAL FIBER PRESSURE TRANSDUCER

[75] Inventor: Donald Cohen, Miami, Fla.

[73] Assignee: Cordis Corporation, Miami, Fla.

[21] Appl. No.: 881,476

[22] Filed: Jul. 1, 1986

Related U.S. Application Data

[63] Continuation of Ser. No. 671,913, Nov. 16, 1984, abandoned.

[51] Int. Cl.$^4$ ............................................. A61B 5/02
[52] U.S. Cl. ................................. 128/667; 128/675;
128/748; 73/705
[58] Field of Search ............... 128/748, 667, 673, 675,
128/634; 73/705; 350/96.32, 96.33; 250/231 P

[56] References Cited

U.S. PATENT DOCUMENTS

| | | | |
|---|---|---|---|
| 3,051,003 | 8/1962 | Witt | 73/705 |
| 3,056,297 | 10/1962 | Duke | 73/705 |
| 3,267,932 | 8/1966 | Vallieve | 128/675 |
| 3,920,312 | 11/1975 | Siegmund | 350/96.32 |
| 4,487,206 | 12/1984 | Aagard | 128/634 X |

Primary Examiner—Kyle L. Howell
Assistant Examiner—John C. Hanley
Attorney, Agent, or Firm—Tarolli, Sundheim & Covell

[57] ABSTRACT

A catheter houses an elongated flexible fiber optic member having a light transmitting core for transmitting light received at its proximal end to its distal end at which the light is reflected back to the proximal end. The fiber optic member is coaxially surrounded by cladding throughout essentially all of its length, except for an uncladded portion of its length adjacent the distal end. A pressure transducer is located adjacent the distal end alongside the uncladded core portion. The transducer is constructed of light absorbing material having a portion thereof making variable surface area contact with the uncladded core portion in dependence upon transversely applied pressure forces. The variations in surface area contact cause changes in the light refraction characteristics. This modulates the intensity of light passing through the core proximate thereto.

8 Claims, 3 Drawing Figures

OPTICAL FIBER PRESSURE TRANSDUCER

This application is a continuation of application Ser. No. 671,913, filed Nov. 16, 1984, now abandoned.

RELATED APPLICATION

This application is related to my previously filed U.S. application Ser. No. 553,581, filed Nov. 21, 1983, entitled "Optical Fiber Pressure Transducer".

BACKGROUND OF THE INVENTION

This invention relates to the art of measuring blood pressure within the cardiovascular system and, more particularly, to apparatus for directly measuring the blood pressure at the location of interest by means of a catheter having a transducer tip insertable into a blood vessel.

Catheters have been used in the art for monitoring variations in blood pressure within the cardiovascular system. It has been accepted practice to insert the distal end of a catheter into a blood vessel and then connect the proximal end of the catheter outside the body, to an external transducer at which pressure variations are measured. Such external transducers are considered relatively inexpensive and employ disposable fluid-filled catheters. However, in use such catheters require periodic flushing to avoid thrombus formation. Also, the frequency response characteristics are often compromised by the mechanical properties of the catheter, inclusion of small air bubbles and by body motion artifact. The blood pressure must be transmitted from the interior of the blood vessel through the catheter tubing by means of the fluid column therein before it can act on the external transducer. Consequently, the frequency response for such an external transducer is also compromised by the relatively large mass of the fluid column within the catheter tubing.

Other approaches to measuring blood pressure have included employing catheter tip transducers insertable into the blood stream. Such catheter tip transducers provide direct pressure monitoring in that they transduce blood pressure at the region of interest rather than attempting to couple the dynamic waveform hydraulically, as in the external transducers. Many of the catheter tip transducers employ semiconductors and other sensing elements of the resistive and/or capacitive variety at the catheter tip. An electrical signal is generated or modulated at the transducer and transmitted through the length of the catheter to meters and the like located externally of the body being tested. Such semiconductor tip transducers are expensive and, hence, the high cost is not compatible with their being disposable units. Instead, there is a tendency to reuse the product and, despite sterilizing or autoclaving, there remains a potential to transfer proteins, which may be antigenic, from one patient to a successive one. Another potentially troublesome feature of such semiconductor tip transducers is the use of electricity to power the sensor. The use of electricity not only renders the device susceptible to electromagnetic interference, but also introduces the possible hazard of arrhythmia induction.

To overcome some of the noted difficulties, other attempts in determining blood pressure in a cardiovascular system have included catheters employing optically based pressure transducers at the distal end. Such devices typically take the form as illustrated in Polyanyi U.S. Pat. No. 3,249,105 and Franke U.S. Pat. No. 3,215,135. Each of these devices employs a catheter having fiber optic means extending the length of the catheter to the distal end thereof at which the fiber optic means is in optical communication with a pressure transducer. The pressure transducers in Polyanyi and Franke, supra, take the form of a diaphragm covering the end hole of the catheter. The diaphragm is located in front or distal to the end of the fiber optical means and then receives light and reflects it back into the fiber optic means for transmission to an externally located meter. Since the transducer is inserted into the blood stream of a patient, the blood pressure deflects the diaphragm causing modulation of the light intensity so that the meter provides an indication of blood pressure.

Such catheters employing diaphragm covered end holes actually measure total pressure rather than the desired measurand; namely, static pressure. Thus, by aligning the end hole of a catheter with the direction of blood flow, kinetic energy terms are introduced. If the catheter end hole is directed upstream, a kinetic term will be added to the pressure, and, if the end hole is facing downstream, the kinetic term will be subtracted from the pressure. The magnitude of the error will vary with flow rate. This error will vary during the course of a cardiac cycle and will distort the shape and magnitude of a pressure wave. In the pulmonary artery, the kinetic pressure may be on the order of 10% of total pressure at rest and 50% of total pressure at a cardiac output equal to three times that at rest. The importance of the kinetic pressure error is particularly great in stenotic areas where velocities are high.

The noted problems with catheters employing diaphragm covered end holes to monitor pressure may be alleviated with a tip transducer that employes side port monitoring of pressure rather than end hole monitoring of pressure. The kinetic contribution is minimal when measuring pressure perpendicular to the blood flow. One such device is known and is reported in a 1978 article entitled "The Development of Fibre Optic Catheter Tip Pressure Transducer", Journal of Medical Technology, Vol. 2, No. 5, by H. Matsumoto and M. Saegusa. As disclosed in that article, the Matsumoto optical sensor employs a tipped transducer having side port monitoring of pressure. The pressure transducer measures pressure acting at right angles to blood flow. A membrane is responsive to the pressure and causes movement of a mirror, which is mounted in cantilevered fashion to the membrane, within a cavity of the transducer. The mirror serves to reflect light received from fiber optic means extending the length of the catheter so that the intensity of light returned by way of the fiber optic means to a measuring device located outside the body is modulated in accordance with the static pressure. However, this structure requires precise alignment between the distal end of the fiber optic means and the cantilevered mounted mirror so that the deflected light, as measured by the externally located meter, will be properly indicative of the static pressure. Additionally, there is a nonlinearity in the response characteristics of such a device both because the cantilevered mounted mirror undergoes an angular displacement and nonlinear displacement.

Another device which may be employed for side port monitoring of blood pressure is illustrated in the E. G. Valliere U.S. Pat. No. 3,267,932. Valliere employs a stress body within a catheter at the distal end thereof. Light from an external source passes through a bundle of optical fibers within the catheter and is then transmitted through the stress body after which the light strikes a reflector and is returned back through the stress body and the catheter to an external meter. The intensity of light returned is modulated in dependence upon pressure applied to the stress body in a direction radially thereof. However, Valliere requires the use of a polarizer so that polarized light components pass back and forth through the stress body. The transmission of the light components is delayed as a function of the stress exerted on the stress body. This serves as a measure of blood pressure.

SUMMARY OF THE INVENTION

It is an object of the present invention to provide an improved optical fiber pressure transducer employing side port measuring of static pressure without the use of stress bodies and polarizers within the distal end of a catheter.

It is a still further object of the present invention to provide an improved optical fiber pressure transducer adapted for side port blood pressure monitoring and which is constructed in a manner so that it is sufficiently inexpensible to be disposable.

It is still further object of the present invention to provide an improved optical fiber pressure transducer employing means at the distal end responsive to blood pressure forces acting transversely of the catheter to vary the intensity of light passing through the optical fiber.

In accordance with the present invention the foregoing objectives are achieved with an optical fiber blood pressure transducer constructed for measuring blood pressure at a remote location within a blood vessel. The apparatus includes an elongated flexible optical fiber having a light transmitting core coaxially surrounded by cladding material essentially throughout its length. The core is uncladded for a portion of its length adjacent its distal end. A pressure transducer is located adjacent the distal end and has at least a portion thereof disposed alongside the uncladded core. The transducer is constructed of flexible light absorbing material having an index refraction greater than that of the core. At least a portion of the transducer has a surface facing the uncladded core and makes surface area contact therewith. This surface area contact increases and decreases respectively with increases and decreases in pressure forces applied transversely of the optical fiber. Consequently, the intensity of light passing by the transducer is modulated inversely proportional to the magnitude of the pressure forces.

In accordance with a more limited aspect of the present invention, the surface of the light absorbing material, as it faces the uncladded core, is irregular so as to make interrupted surface area contacts with the uncladded core. These surface area contacts are separated by pockets of air. As the pressure forces vary, the areas of surface contact increase and decrease.

Still further in accordance with a more limited aspect of the present invention, the transducer is an annular ring of porous sponge-like material which coaxially surrounds a portion of the length of the uncladded core at the distal end.

BRIEF DESCRIPTION OF THE DRAWINGS

The foregoing and other objects and advantages of the present invention will become more apparent from consideration of the following description as taken in conjunction with the accompanying drawings, wherein.

DETAILED DESCRIPTION OF PREFERRED EMBODIMENT

Figure 1:
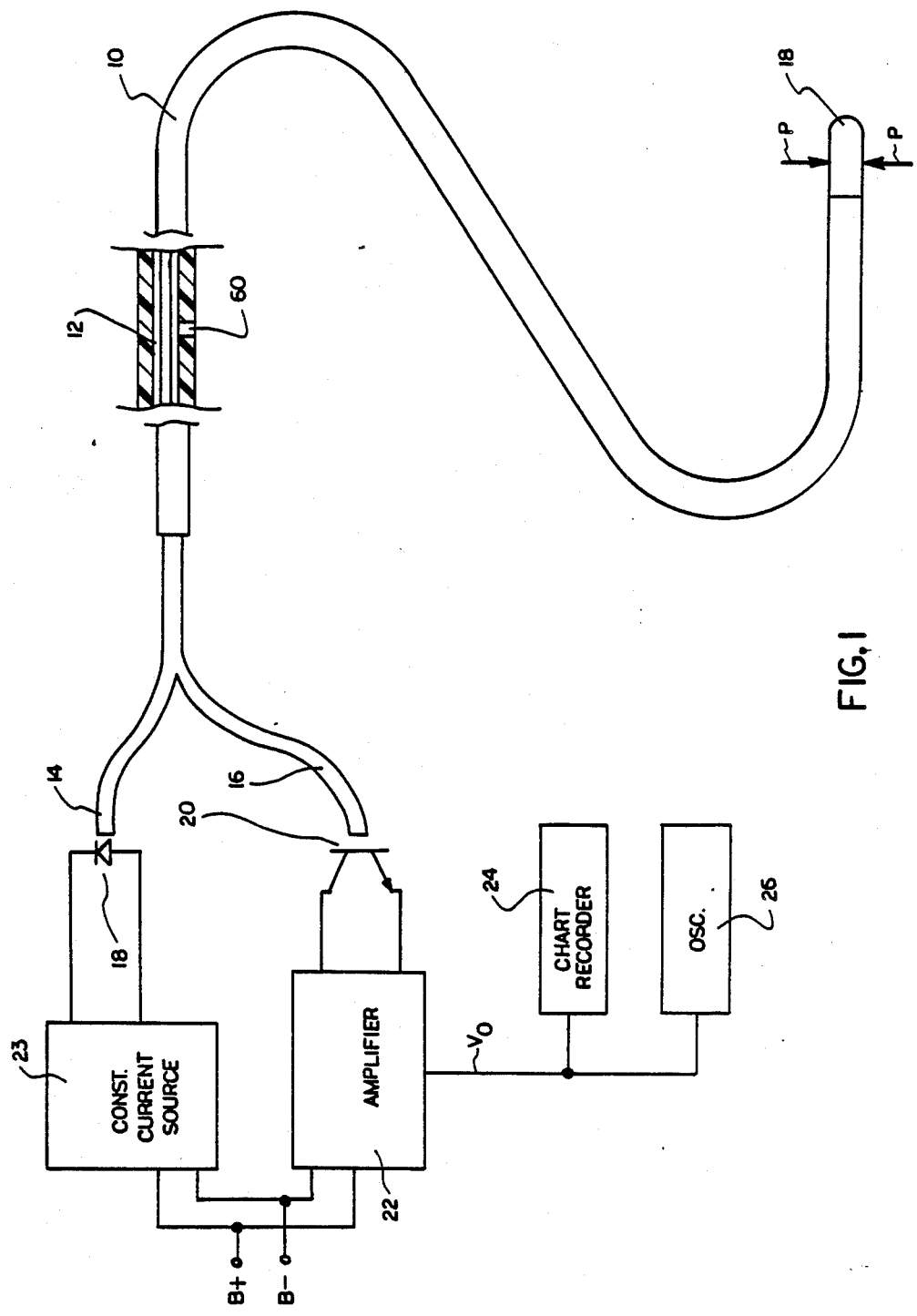
FIG. 1 is a schematic illustration of the catheter in conjunction with one application of this invention.

Reference is now made to the drawings wherein the showings are for purposes of illustrating a preferred embodiment only, and not for limiting same. FIG. 1 illustrates an application of the invention as applied to measurement of pressure within a patient's cardiovascular system and includes an elongated single lumen catheter 10 containing an optical fiber 12 which extends throughout the length of the catheter. The optical fiber 12 is bifurcated at its proximal end defining two legs 14 and 16. Leg 14 is positioned to receive light from an ultra bright light emitting diode (LED) 18 for transmission through the length of fiber 12 to its distal end at which there is located a pressure transducer 18. The transducer 18 is responsive to pressure forces acting transversely of the optical axis and these forces are represented by the arrows P in FIG. 1. As will be brought in greater detail, light transmitted by way of the optical fiber through the transducer 18 is modulated in its intensity inversely proportional to the pressure and the intensity modulated light travels back through the optical fiber 12 and then through leg 16 and is sensed by a photodiode 20.

The photodiode 20 is connected with suitable circuitry, including an amplifier 22 for providing an output voltage $V_0$ having a magnitude which varies in dependence upon the amount of current flowing through the photodiode and which, in turn, varies with the amount of light it receives from the optical fiber leg 16. The output voltage $V_0$ from the amplifier may then be supplied to a suitable readout, such as a chart recorder 24 and an oscilloscope 26. Other outputs including digital voltmeters and the like may be employed as desired.

The bifurcated distal end together with the electronics, including light emitting diode 18 and a constant current source 23, the photodiode 20, amplifier 22 and readout meters may all take the form as described and illustrated in the aforesaid related application, U.S. Ser. No. 553,581, which was filed on Nov. 21, 1983. As brought out therein, constant current on the order of 30 milliamps is supplied to the light emitting diode 18 having a power dissipation of approximately 60 milliwatts. The photodiode 20 may take the form of a silicon PIN (Positive Intrinsic Negative) photodiode. The sensitivity of the photodiode 20 is on the order of one ampere per watt. The amplifier has a gain adjustment for varying the magnitude of the output voltage $V_0$. Additionally, an offset adjustment is provided for an initial zeroing operation.

Figure 2:
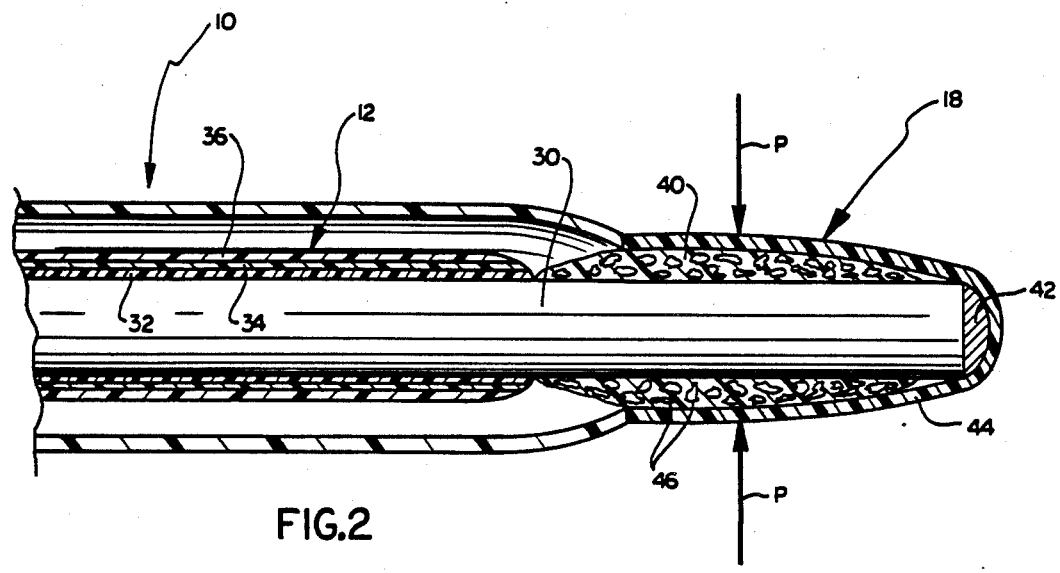
FIG. 2 is an enlarged cross-sectional view of the transducer.

Having described the application of the invention as presented in FIG. 1, attention is now directed to a more detailed description of the transducer 18 in connection with FIG. 2. In FIG. 2, the transducer 18 is enlarged in size for ease in understanding the construction. The catheter 10 is a single lumen, thin walled catheter such as that provided by Cordis Corporation, and known as a Cordis FR5 thin wall catheter. This catheter may have a diameter on the order of 0.066 inches and is constructed of plastic material such as polyurethane.

The catheter carries the optical fiber 12, taking the form in the preferred embodiment of FIG. 2 of a cladded single optical fiber. This fiber has a core 30 of acrylic material of a maximum diameter on the order of 368 micra. The core 30 is covered throughout essentially all of its length with cladding 32 constructed of a fluoropolymer having a thickness on the order of 16 micra. Surrounding the cladding 32 are Kevlar strands 34 for purposes of strengthening the optical fiber 30. Tte Kevlar strands 34 are, in turn, covered with a layer of black Hytrel 36.

Such optical fibers are available commercially as from Dupont Corporation of Wilmington, Delaware.

The cladding 32, strands 34 and coating 36 are removed from the distal end and replaced with a sponge-like annular transducer ring 40. The distal end of the core is coated with a reflective material to define a reflective surface 42. A protective membrane 44 extends from the distal end of the catheter and covers the annular transducer ring 40 and the reflective surface 42, as seen in FIG. 2.

The removal of the cladding 32 may be accomplished in a controlled manner as with the use of a solvent, such as tetrahydrofluran, so that the removal takes place only at the tip of the optical fiber. The annular transducer ring 40 that encircles the uncladded end of the fiber is a sponge-like material, such as polyurathane foam. This may take the form of hypol foamable hydrophilic polyurathane polymer which may be obtained from the organic chemicals division of the W. R. Grace & Company. This is a porous material and includes interconnecting pores 46. The transducer ring 40 encircles the distal tip end of the uncladded core and is held in place as by an interference fit. The membrane 44 is of latex material and may be formed by dipping the distal end of the catheter, with the transducer ring 40 in place, into a viscous liquid of latex and then air drying it. The membrane, while covering the distal end of the catheter, will adhere and form a seal with the catheter, but does not adhere to the sponge-like material forming the transducer ring 40. The mirrored end or reflective coating 42 may be of suitable reflective material, such as silver and the like (but not confined to metals), which is deposited on the distal tip end of the core 30 by sputtering, use of a colloidal material or transparent adhesive. The interior walls of the lumen at the distal end of the catheter may be coated with optically black material.

Figure 3:
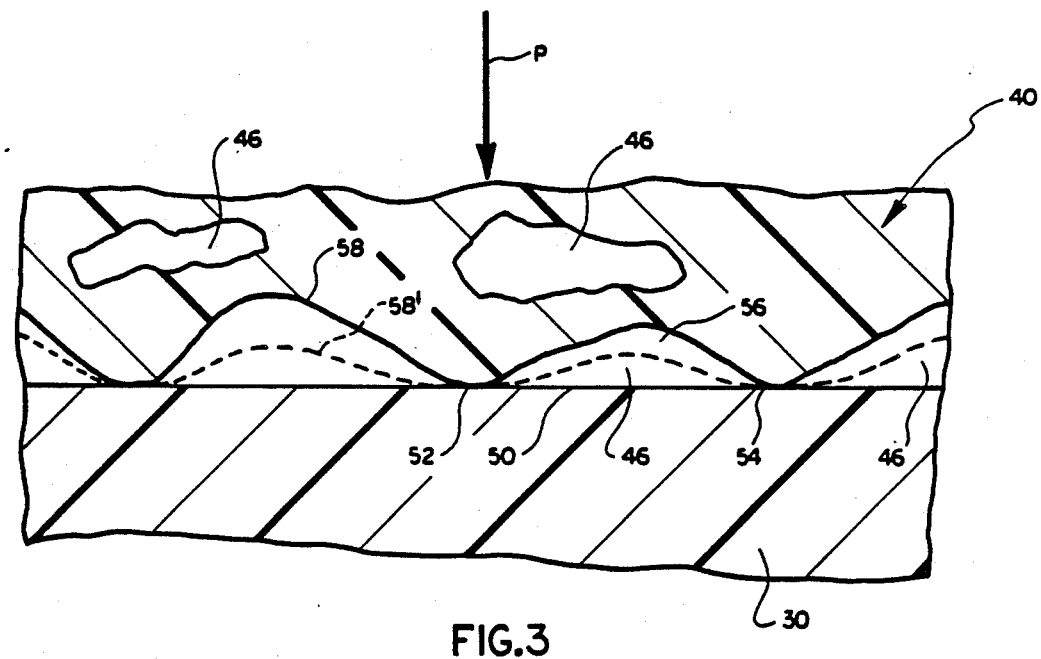
FIG. 3 is an enlarged view showing a portion of the transducer in surface engagement with the uncladded core.

Reference is now made to FIG. 3 which is an enlarged showing of a portion of the length of the uncladded optical fiber core 30 in engagement with a portion of the transducer ring 40. The transducer material is sponge-like and has interconnected pores 46. Consequently, transducer ring 40 makes interrupted surface areas contacts with the relatively smooth, uncladded surface 50 of the fiber core 30. As seen in FIG. 3, the transducer ring 40 makes surface engagement with the core surface 50 at various locations, such as 52 and 54, separated by an air pocket 56. This defines a pitted interior surface 58. The air pockets 56 are vented to the atmosphere by way of pores 46 and the annular space surrounding the cladded core within the lumen of the catheter 10 which leads to an aperture 60 located at the proximal end of the catheter. This, then, provides the basis for a pressure differential with externally applied pressure forces P. As the pressure P increases, the interior surface 58 of ring 40 will move toward the uncladded surface 50, as indicated by the dotted lines 58', so as to increase the surface area contact with the uncladded surface 50. Likewise, as the pressure forces are removed, the sponge-like material, being resilient, will return to that as indicated by the solid line 58 in FIG. 3 and make less surface area contact with the uncladded surface 50. These variations in surface area contact between the transducer 40 and the uncladded surface of the optical fiber core 30 with variations in pressure forces P modulates the intensity of light travelling through the optical fiber.

At this point, it is to be noted that the index of refraction n is different for the various materials employed. Thus, the index of the refraction n for the fiber core 30 is on the order of 1.5, and that for the surrounding air within the air pockets 46 and in the lumen, as vented to the atmosphere, is on the order of 1.0. The cladding 32 exhibits an index of refraction n of 1.4 which is slightly less than that of the core 30. The index of refraction of the sponge-like material forming the transducer ring 40 is greater than that of the cladding 32 and that of the fiber core 30.

Light that travels through the core 30 and which strikes the core-air interface will be totally internally reflected. However, light that strikes the core-sponge interface will be partially refracted and partially reflected. The amount of light that is refracted, and, hence, absorbed will be a function of the surface contact area. Thus, light that is travelling from the proximal end to the distal end of the catheter will pass through the transducer area and a portion of the light will be absorbed in dependence upon the pressure P. The light that is internally reflected will be reflected back by the reflector surface 42. This reflected back light will also be attenuated as it passes the transducer area as it travels back toward the proximal end of the catheter. Consequently, then, the intensity of light returning at the proximal end of the catheter at the fiber leg 16 will vary inversely with the pressure forces P applied to the transducer. This is sensed by the photodiode 20 and amplified by amplifier 22 to provide an operator with a readout as with a chart recorder 234 or an oscilloscope 26.

It is suggested that the instrumentation be zeroed or calibrated prior to insertion of the catheter into a patient. Thus, it is contemplated that the instrumentation associated with the amplifier 22 include means for adjusting the gain so as to vary the magnitude of the output voltage $V_0$ with respect to a particular pressure reading. It is also contemplated that the amplifier circuitry include zeroing adjustment means, such as a potentiometer, to zero out the effects of any back reflection, as from the optical fiber leg 14 to the optical fiber leg 16. This adjustment may apply an offsetting bias so that the output voltage $V_0$ is equal to zero when the applied pressure P is equal to atmospheric pressure.

With the preliminary adjustments being made, the operator may now insert the distal end of the catheter 10 into a blood vessel, such as the pulmonary artery, of the patient, until the transducer tip reaches the site of interest. The aperture 60 at the proximal end of the catheter should be external of the patient's body so that atmospheric pressure is communicated through the lumen of the catheter to the pores 46 of the annular transducer ring 40. Pressure, greater than atmospheric, exerted in the direction P will cause deflection of the sponge-like material so as to increase the area of surface contact with the uncladded surface 50 of core 30. Conversely, pressure less than atmospheric will result in a decrease in the contact area. With the distal end in place and power turned on, light emitted from diode 18 will be transmitted by way of the optical fiber leg 16 and then through the core 30 to the distal end of the catheter where the intensity of the light will be modulated in dependence upon the pressure acting on the annular ring 40.

In the embodiment described with reference to FIGS. 1-3, a sponge-like material has been employed as the transducer annular ring 40. It is contemplated that such sponge-like material will have interconnecting pores 40 so that they may be in communication with atmospheric pressure by way of the lumen within the catheter leading to the aperture 60 at the proximal end. The above described annular ring is held on to the uncladded core 30 at the distal end by an interference fit. Alternatively, the sponge-like material could be molded in place onto the uncladded core at the distal end. Also, instead of employing sponge-like material, the effect of an irregular surface which can make varying surface area contact in dependence upon transversely directed pressure forces P may be achieved with a spirally wound plastic, or a woven material placed against the uncladded surface of the core.

Although the invention has been described in conjunction with a preferred embodiment, it is to be appreciated that various modifications may be made without departing from the spirit and scope of the invention as defined by the appended claims.

Having described a preferred embodiment of the invention, the following is claimed:

1. Apparatus for use in measuring blood pressure at a remote location within a blood vessel and comprising:
    an elongated flexible fiber optic member of a size sufficiently small to be inserted into a said blood vessel and having a light transmitting core coaxially surrounded by cladding means essentially throughout its length, said core being uncladded for a portion of its length adjacent the distal end thereof;
    pressure transducer means located adjacent said distal end alongside said uncladded portion, said transducer means being constructed of flexible light absorbing porous material having an index of refraction greater than that of said cladding means and having a pitted surface portion facing said uncladded core portion making interrupted multiple surface area contact therewith throughout the area that said surface portion faces said uncladded portion such that the total surface contact area varies with pressure forces applied to said transducer means acting transversely of said uncladded core portion whereby the intensity of any light passing through said core portion proximate to said contact surface area can be modulated inversely proportional to the magnitude of said pressure forces, said porous material having interconnected pores of sufficient size to vent air from locations between said uncladded core portion and said pitted surface portion.

2. Apparatus as set forth in claim 1 including reflective means located at the distal end of said core for reflecting light received back toward the proximal end of said core.

3. Apparatus as set forth in claim 1 including means for communicating said porous material with atmospheric pressure.

4. Apparatus as set forth in claim 3 wherein said communicating means includes an elongated catheter which coaxially surrounds the length of at least said cladded portion and defining an annular passageway therebetween for providing an air passageway.

5. Apparatus as set forth in claim 4 wherein said catheter housing includes an aperture at its proximal end for communicating atmospheric pressure to said porous material by way of said air passageway.

6. Apparatus as set forth in claim 5 wherein said transducer means has an outer surface, and nonporous means for sealing said outer surface of said transducer means.

7. Apparatus as set forth in claim 6 wherein said sealing means includes a flexible diaphragm for transmitting said transverse pressure forces to said porous material.

8. Apparatus as set forth in claim 7 wherein said diaphragm covers the distal end of said core so as to encase the transducer means between said diaphragm means and said uncladded core portion.

* * * * *